US010466172B2

(12) United States Patent
Yaman et al.

(10) Patent No.: US 10,466,172 B2
(45) Date of Patent: *Nov. 5, 2019

(54) DISTRIBUTED ACOUSTIC SENSING IN A MULTIMODE OPTICAL FIBER USING DISTRIBUTED MODE COUPLING AND DELAY

(71) Applicant: NEC Laboratories America, Inc., Princeton, NJ (US)

(72) Inventors: Fatih Yaman, Princeton, NJ (US); Giovanni Milione, Franklin Square, NJ (US); Shaoliang Zhang, Princeton, NJ (US); Yue-Kai Huang, Princeton, NJ (US)

(73) Assignee: NEC Corporation (JP)

( * ) Notice: Subject to any disclaimer, the term of this patent is extended or adjusted under 35 U.S.C. 154(b) by 247 days.

This patent is subject to a terminal disclaimer.

(21) Appl. No.: 15/678,656

(22) Filed: Aug. 16, 2017

(65) Prior Publication Data

US 2018/0052041 A1 Feb. 22, 2018

Related U.S. Application Data

(60) Provisional application No. 62/377,784, filed on Aug. 22, 2016, provisional application No. 62/377,730, filed on Aug. 22, 2016.

(51) Int. Cl.
*G01H 9/00* (2006.01)
*G01K 11/32* (2006.01)
(Continued)

(52) U.S. Cl.
CPC ............. *G01N 21/47* (2013.01); *G01H 9/004* (2013.01); *G01K 11/32* (2013.01);
(Continued)

(58) Field of Classification Search
CPC ........ G01H 9/004; G01K 11/32; G01N 21/47; G01N 2021/432; G01N 2021/638;
(Continued)

(56) References Cited

U.S. PATENT DOCUMENTS 5,696,863 A   12/1997 Kleinerman
9,077,577 B1 * 7/2015 Ashrafi ................ H04L 27/362
(Continued)

OTHER PUBLICATIONS

70-Gb/s Multicore Multimode Fiber Transmissions, Benyuan Zhu et al., IEEE Photonics Technology Letters, vol. 22, No. 22, Nov. 15, 2010.*

(Continued)

*Primary Examiner* — Jacques M Saint Surin
(74) *Attorney, Agent, or Firm* — Joseph Kolodka

(57) ABSTRACT

A system and method are provided for distributed acoustic sensing in a multimode optical fiber. The system includes a transmitter for simultaneously propagating a sequence of M light pulses through the multimode optical fiber using a spatial mode selected from a set of N spatial modes provided by a spatial mode selector for the transmitter that is coupled to an input to the multimode optical fiber, with M and N being respective integers greater than one. The system further includes a receiver for receiving the sequence of M light pulses at an output of the multimode optical fiber and detecting an environmental perturbation in the multimode optical fiber based on an evaluation of a propagation of the sequence of M light pulses through the multimode optical fiber.

20 Claims, 12 Drawing Sheets

(51) Int. Cl.
*G02B 6/02* (2006.01)
*G01M 11/08* (2006.01)
*G01N 21/47* (2006.01)
*G01N 21/17* (2006.01)
*G01N 21/43* (2006.01)
*G01N 21/63* (2006.01)

(52) U.S. Cl.
CPC ........ *G01M 11/083* (2013.01); *G01M 11/085* (2013.01); *G02B 6/02042* (2013.01); *G01N 2021/1744* (2013.01); *G01N 2021/432* (2013.01); *G01N 2021/638* (2013.01)

(58) Field of Classification Search
CPC ....... G01N 2021/1744; G01M 11/3172; G02B 6/02042
USPC .......................................................... 73/643
See application file for complete search history.

(56) References Cited

U.S. PATENT DOCUMENTS

| 10,018,558 | B2* | 7/2018 | Yaman | G01H 9/004 |
| 2010/0207019 | A1* | 8/2010 | Hartog | E21B 47/101 |
| | | | | 250/269.1 |
| 2012/0262780 | A1 | 10/2012 | Bai et al. | |
| 2013/0230311 | A1* | 9/2013 | Bai | H04B 10/2581 |
| | | | | 398/9 |
| 2014/0208855 | A1* | 7/2014 | Skinner | G01H 9/004 |
| | | | | 73/655 |
| 2014/0224033 | A1* | 8/2014 | Froggatt | G01L 1/246 |
| | | | | 73/800 |
| 2015/0116124 | A1 | 4/2015 | Jaaskelainen et al. | |
| 2015/0146759 | A1 | 5/2015 | Johnston | |
| 2017/0167899 | A1* | 6/2017 | Amezcua-Correa | |
| | | | | G01K 11/3206 |
| 2017/0211970 | A1* | 7/2017 | Milione | G01H 9/004 |

OTHER PUBLICATIONS

Alekseev, et al., "Contrast Enhancement in an Optical Time-Domain Reflectometer Via Self-Phase Modulation Compensation by Chirped Probe Pulses", IPO Publishing, Astro Ltd., Laser Physics, Feb. 2016, 8 pages.
Bao et al., "Recent Progress in Distributed Fiber Optic Sensors", Sensors, Open Access, Jun. 2012, 39 pages.
Iida, et al., "High-Frequency Distributed Acoustic Sensing Faster Than Repetition Limit With Frequency-Multiplexed Phase-OTDR", IEEE Explore, Mar. 2016, 3 pages.
Johannessen, et al., "Distributed Acoustic Sensing—A New Way of Listening to Your Well/Reservoir", SPE International, Mar. 2012, pp. 1-9.
Martins, et al., "Phase-sensitive Optical Time Domain Reflectometer Assisted by First-order Raman Amplification for Distributed Vibration Sensing Over >100 km", Journal of Lightwave Technology, Apr. 2014, pp. 1510-1518, vol. 32, No.8.
Muanenda, et al.,"A Cost-Effective Distributed Acoustic Sensor Using a Commercial Off-the-Shelf DFB Laser and Direct Detection Phase-O", IEEE Photonics Journal, Feb. 2016, 11 pages, 11 pages.

* cited by examiner

DISTRIBUTED ACOUSTIC SENSING IN A MULTIMODE OPTICAL FIBER USING DISTRIBUTED MODE COUPLING AND DELAY

RELATED APPLICATION INFORMATION

This application claims priority to U.S. Provisional Pat. App. Ser. No. 62/377,784, filed on Aug. 22, 2016, incorporated herein by reference herein its entirety. This application also claims priority to U.S. Provisional Pat. App. Ser. No. 62/377,730, filed on Aug. 22, 2016, incorporated herein by reference herein its entirety. This application is related to an application entitled "Distributed Acoustic Sensing in a Multicore Optical Fiber Using Distributed Mode Coupling and Delay", Ser. No. 15/678,728, and which is incorporated by reference herein in its entirety.

BACKGROUND

Technical Field

The present invention relates to telecommunication systems and more particularly to distributed acoustic sensing in a multimode optical fiber using distributed mode coupling and delay.

Description of the Related Art

Distributed fiber sensing (DFS) is the use of an optical fiber to sense environmental perturbations (e.g., acoustic vibration, changes in pressure, changes in temperature, etc.) along the optical fiber's length. The length of the optical fiber can be as short as 1 meter and as long as 100 of kilometers. Conventional methods of DFS exploit various light-matter interaction-based physical mechanisms in the optical fiber. For example, distributed acoustic sensing (DAS) exploits Rayleigh scattering to sense acoustic vibrations, distributed Brillouin sensing exploits Brillouin scattering to sense strain and temperature, and distributed Raman sensing exploits Raman scattering to sense temperature.

In particular, Distributed Acoustic Sensing (DAS) has received particular interest in recent years. As compared to point sensors, due its distributiveness, DAS can better monitor, for example, terrestrial and undersea oil and gas wells/pipelines, thereby enabling longer oil and gas well/pipeline lifetimes and, in turn, better optimizing associated financial revenue.

In conventional methods of DAS, a laser pulse is launched into the optical fiber input and creates Rayleigh scattering as it propagates along the optical fiber's length. Using a time of flight analysis, referred to as optical time domain reflectometry (OTDR), at the optical fiber input, Rayleigh backscattering is measured at continuous points along the optical fiber's length. As a result, each point of the resulting OTDR "trace" corresponds to a unique spatial position z along the optical fiber's length, i.e., each spatial z point along the optical fiber's length can be discriminated unambiguously. Via the photo-elastic effect, if an acoustic vibration makes physical contact with the optical fiber at some point(s) along its length, the phase of the Rayleigh backscattering will change proportionally. Effectively, by measuring the phase of the Rayleigh backscattering in concert with the time of flight analysis, a signal of the acoustic vibration(s) (i.e. amplitude and frequency) can be sensed at any point along the optical fiber's length.

While effective, fundamental problems of conventional methods of DAS include the following.

Problem 1—Detection Speed:

The detection speeds of conventional methods of DAS are limited. The limited detection speeds of conventional methods of DAS are due to the fact that only one laser pulse can occupy the optical fiber at any given time so that a unique spatial position of the optical fiber can be discriminated unambiguously via the Rayleigh backscattering's time of flight analysis. Therefore, the maximum detection speed, and, via the Nyquist sampling limit, the maximum detectable frequency, is limited by the laser pulse's round trip time of flight.

Problem 2—Distance:

Conventional methods of DAS rely on Rayleigh scattering. Relative to the power of the launched laser pulse, Rayleigh scattering is orders of magnitude weaker. Additionally, as a light pulse propagates along an optical fiber, the power of the light pulse will attenuate. As a result, at some point along the optical fiber, the already relatively weak power Rayleigh scattering will have a signal to noise ratio that makes the desired acoustic vibration undetectable. Therefore, the length of optical fiber (distance) over which DAS can be used is limited.

Problem 3—Sensitivity:

Conventional methods of DAS exploit Rayleigh scattering. Relative to the power of the launched laser pulse, Rayleigh scattering is orders of magnitude weaker. As a result, the signal to noise ratio of the sensed acoustic vibration is dominated by optical noise due to for example the frequency noise of the laser pulse, the limited extinction ratio of the laser pulse, optical amplification noise, and detector noise. In turn, the sensitivity of conventional methods of DAS, i.e., the maximum detectable vibration amplitude, is limited, in turn, precluding detection of sensitive phenomena in gas and oil wells, such as, micro-seismic activity.

Accordingly, there is a need for distributed acoustic sensing in a multimode optical fiber using distributed mode coupling and delay.

SUMMARY

According to an aspect of the present invention, a system is provided for distributed acoustic sensing in a multimode optical fiber. The system includes a transmitter for simultaneously propagating a sequence of M light pulses through the multimode optical fiber using a spatial mode selected from a set of N spatial modes provided by a spatial mode selector for the transmitter that is coupled to an input to the multimode optical fiber, with M and N being respective integers greater than one. The system further includes a receiver for receiving the sequence of M light pulses at an output of the multimode optical fiber and detecting an environmental perturbation in the multimode optical fiber based on an evaluation of a propagation of the sequence of M light pulses through the multimode optical fiber.

According to another aspect of the present invention, a computer-implemented method is provided for distributed acoustic sensing in a multimode optical fiber. The method includes simultaneously propagating, by a transmitter, a sequence of M light pulses through the multimode optical fiber using a spatial mode selected from a set of N spatial modes provided by a spatial mode selector coupled to an input to the multimode optical fiber, with M and N being respective integers greater than one. The method further includes detecting, by a receiver, an environmental perturbation in the multimode optical fiber based on an evaluation of a propagation of the sequence of M light pulses through the multimode optical fiber.

According to yet another aspect of the present invention, a computer program product is provided for distributed acoustic sensing in a multimode optical fiber. The computer program product includes a non-transitory computer readable storage medium having program instructions embodied therewith. The program instructions are executable by a computer to cause the computer to perform a method. The method includes simultaneously propagating, by a transmitter, a sequence of M light pulses through the multimode optical fiber using a spatial mode selected from a set of N spatial modes provided by a spatial mode selector coupled to an input to the multimode optical fiber, with M and N being respective integers greater than one. The method further includes detecting, by a receiver, an environmental perturbation in the multimode optical fiber based on an evaluation of a propagation of the sequence of M light pulses through the multimode optical fiber.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
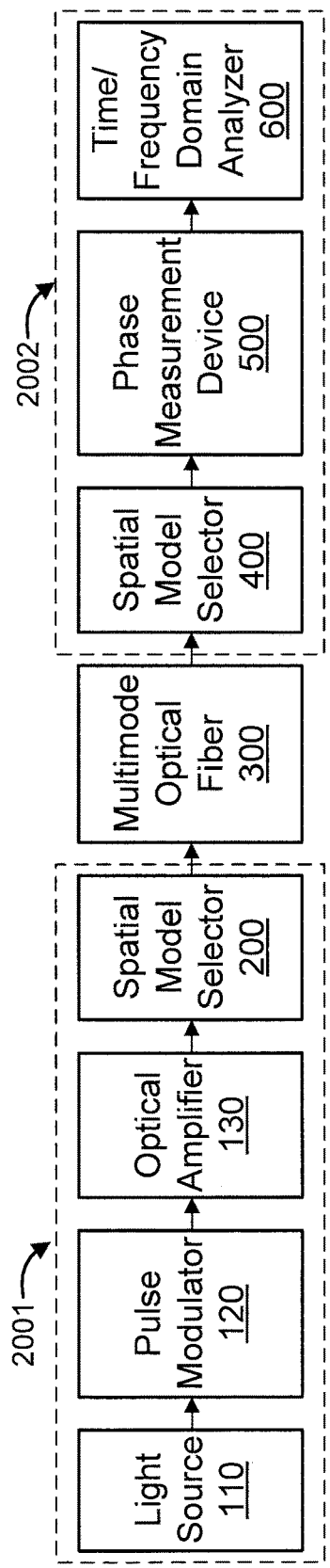
FIG. 1 shows an exemplary system for distributed acoustic sensing in a multimode optical fiber using Distributed Mode Coupling and Delay, in accordance with an embodiment of the present invention.

The present invention is directed to distributed acoustic sensing in a multimode optical fiber using distributed mode coupling and delay.

The problems described above are due to the reliance of conventional methods of DAS on Rayleigh backscattering. The present invention solves the problems described above because the present invention does not rely on Rayleigh backscattering. Instead, in an embodiment, the present invention relies on distributed mode coupling and distributed mode delay.

The following advantages are provided by the present invention with respect to the aforementioned problems of the prior art.

Increased Detection Speed: Because conventional methods of DAS rely on Rayleigh scattering, only one laser pulse can propagate along the optical fiber at any given time. As a result, according to the Nyquist sampling limit, the maximum detectable frequency of an acoustic vibration is proportional to the round trip time of flight of a laser pulse through the optical fiber.

However, because the present invention does not rely on Rayleigh scattering, multiple laser pulses can simultaneously propagate inside the optical fiber. As will be described below, the number of laser pulses that can simultaneously propagate inside the optical fiber is determined by the differential mode delay between the spatial modes. The differential mode delay between the spatial modes is significantly less than the round trip time of flight of a laser pulse through the optical fiber even when the optical fiber is 10s of meters long. Therefore, the maximum detectable frequency of an acoustic vibration via the present invention can be many orders of magnitude more than conventional methods of DAS. The present invention is a method of DAS whose detection speed can be orders of magnitude more than conventional methods of DAS.

Increased Distance:

Relative to the power of the launched laser pulse, Rayleigh scattering is orders of magnitude weaker. Additionally, as a light pulse propagates along an optical fiber, the power of the light pulse will attenuate. As a result, at some point along the optical fiber, the already relatively weak power Rayleigh scattering will result in an insufficient signal to noise ratio. Therefore, the length of optical fiber (distance) over which DAS can be used is limited.

However, the present invention does not rely on Rayleigh scattering. The present invention relies on distributed mode coupling. The relative power of mode coupling to the laser pulse is orders of magnitude more than that of Rayleigh scattering. As a result, the signal to noise ratio of the present invention is order of magnitude more than that of conventional methods of DAS. In turn, with the present invention, the length of optical fiber (distance) over which DAS can be used may be orders of magnitude more than that of conventional methods of DAS.

Increased Sensitivity:

Relative to the power of the launched laser pulse, Rayleigh scattering is orders of magnitude weaker. Additionally, as a light pulse propagates along an optical fiber, the power of the light pulse will attenuate. As a result, for a fixed length of optical fiber, the signal to noise ratio of the sensed acoustic vibration is dominated by optical noise due to for example the frequency noise of the laser pulse, the limited extinction ratio of the laser pulse, optical amplification noise, and detector noise. In turn, the sensitivity of conventional methods of DAS, i.e., the maximum detectable vibration amplitude, is limited, in turn, detection of sensitive phenomena in gas and oil wells, such as, micro-seismic activity, is precluded.

However, the present invention does not rely on Rayleigh scattering. The present invention relies on distributed mode coupling. The relative power of mode coupling to the laser pulse is orders of magnitude more than that of Rayleigh scattering. As a result, the signal to noise ratio of the present invention may not be dominated by optical noise due to for example the frequency noise of the laser pulse, the limited extinction ratio of the laser pulse, optical amplification noise, and detector noise. As a result, the present invention is a method of DAS that has far greater sensitivity than conventional methods of DAS.

Referring to FIG. 1, an exemplary system for distributed acoustic sensing in a multimode optical fiber using Distributed Mode Coupling and Delay is shown, in accordance with an embodiment of the present invention.

The system includes a light source 110, a pulse modulator 120, an optical amplifier 130, a spatial mode selector 200, a multimode optical fiber 300 including N spatial modes, a spatial mode selector 400, a phase measurement device 500, and a time/frequency domain analyzer 600.

The light source 110, pulse modulator 120, optical amplifier, and spatial mode selector 200 can be considered to correspond to a transmitting side or transmitter 2001. The spatial mode selector 400, the phase measurement device 500, and the time/frequency domain analyzer 600 can be considered to correspond to a receiving side or receiver 2002. The multimode optical fiber 300 is the propagation medium.

The elements of FIG. 1 are described in further detail hereinafter.

Figure 2:
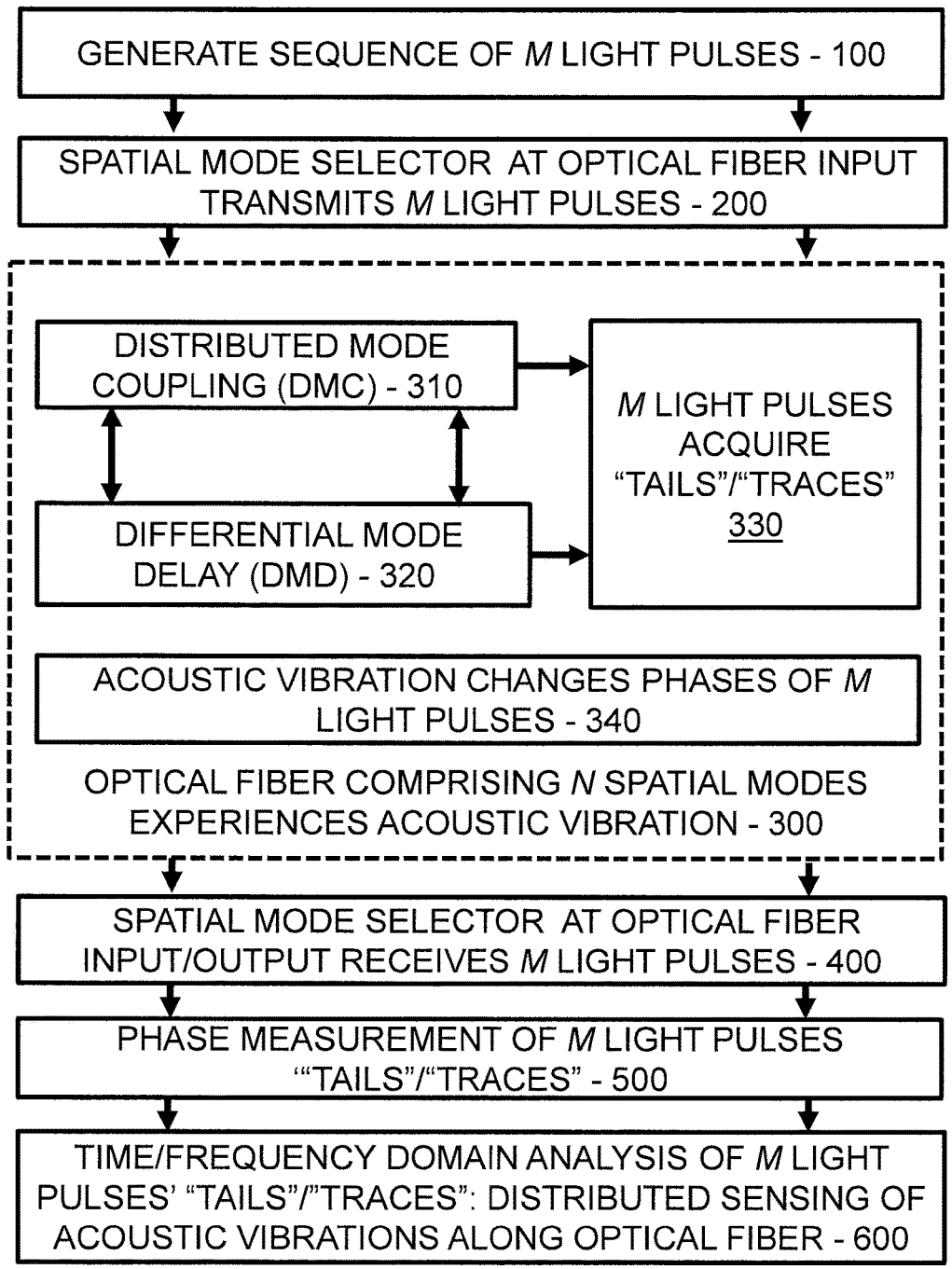
FIG. 2 shows an exemplary method for distributed acoustic sensing in a multimode optical fiber using Distributed Mode Coupling and Delay, in accordance with an embodiment of the present invention.

Referring to FIG. 2, an exemplary method for distributed acoustic sensing in a multimode optical fiber using Distributed Mode Coupling and Delay is shown, in accordance with an embodiment of the present invention.

At step 100, generate a sequence of M light pulses.

At step 200, transmit the sequence of M light pulse using the spatial mode selector at the optical fiber input.

At step 300, experience acoustic vibration, by the optical fiber comprising N spatial modes.

In an embodiment, step 300 includes steps 310, 320, 330, and 340.

At step 310, perform Distributed Mode Coupling (DMC).

At step 320, perform Differential Mode Delay (DMD).

At step 330, acquire "tails"/"traces", by the M light pulses.

At step 340, change the phases of the M light pulses, by the acoustic vibration.

At step 400, receive the M light pulses, by the spatial mode selector at the optical fiber input/output.

At step 500, perform a phase measurement of the M light pulses "tails"/"traces".

At step 600, perform a time/frequency domain analysis of the M light pulses "tails"/"traces" using distributed sensing of acoustic vibrations along optical fiber.

A further detailed description will now be given regarding various aspects of the present invention, in accordance with one or more embodiments of the present invention.

Initially, a further description will now be given regarding step 100 of FIG. 2. The description will be made with referring to both FIGS. 1 and 2.

As noted above, step 100 involves generating M light pulses. However, it is to be appreciated that continuous wave light can also be used when using, for example, well-known optical frequency domain reflectometry methods.

Step 100 of FIG. 1 involves light source 110, pulse modulator 120, and optical amplifier 130.

The light source, also referred to as "pulse generator", 110 is used to generate light. The light source 110 can be any of the following: a coherent laser (diode, solid state, gas, optical fiber, semiconductor, etc.), and so forth.

The wavelength(s) of the light source 110 can be any wavelength(s) that is(are) guided in the optical fiber (e.g. visible, near-infrared, etc.).

The pulse modulator (which can be implemented by the light source/pulse generator) 120 temporally modulates the light source such that it is a sequence of M light pulses. The pulse width and the repetition rate of the light pulses are controlled by the pulse modulator 120. The repetition rate of the light pulses does not have to be the round trip time of flight of one light pulse through an optical fiber. The pulse modulator 120 can be any of the following: (1) Acoustic-Optic Modulator (AOM); (2) Semiconductor Optical Amplifier (SOA); (3) Mach-Zender modulator; (4) Mechanical modulator ("Fan"/"Chopper"); (5) and so forth.

The optical amplifier 130 is used to amplify the power of the M laser pulses. The optical amplifier can be any of the following: (1) Erbium Doped Fiber Amplifier (EDFA); (2) Semiconductor Optical Amplifier (SOA); (3) Raman amplification; and (4) so forth.

The spatial mode selector 200 converts the M light pulses into one spatial mode or a superposition of N spatial modes and then transmits the spatial mode(s) into an optical fiber that supports N spatial modes. The conversion can be performed, for example, using free space optics and/or fiber optics.

A spatial mode 210 is defined as follows. Spatial modes are propagation states of light being orthogonally discriminated by space and/or polarization that are solutions to a wave equation that describes light propagation in an optical fiber in any coordinate system (e.g., Cartesian, cylindrical, etc.). Spatial modes can be (1) transverse modes of a multimode optical fiber such as the following 211: (1A) Hermite-Gaussian modes 211-1; (1B) Laguerre-Gaussian modes; (1C) "Linearly Polarized" modes; (1D) vector modes; and (1E) so forth.

Figure 3:
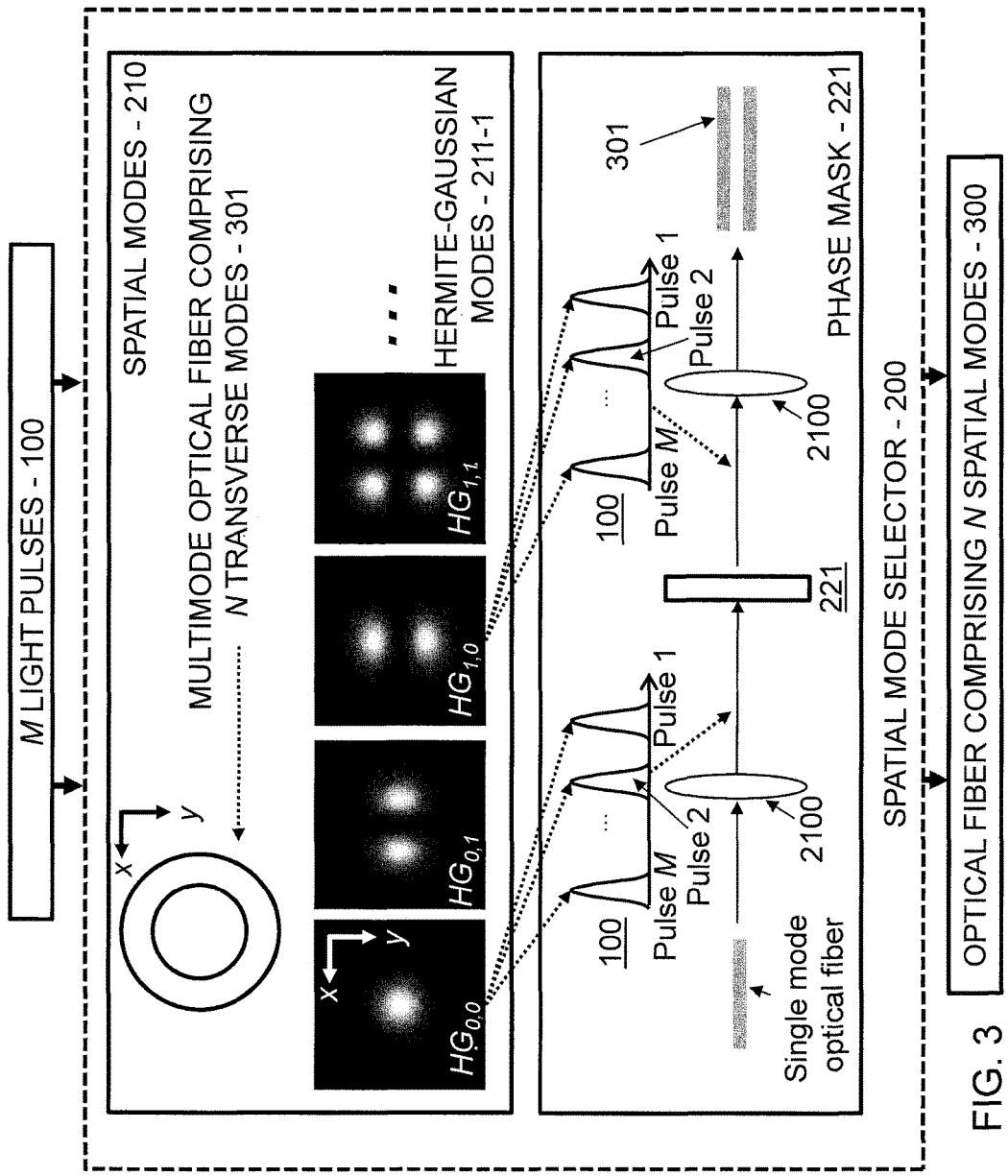
FIG. 3 shows an example of Digital Acoustic Sensing (DAS) using a spatial mode selector based on phase mask conversion, in accordance with an embodiment of the present invention.

Referring to FIG. 3, an example of Digital Acoustic Sensing (DAS) using a spatial mode selector based on phase mask conversion is shown, in accordance with an embodiment of the present invention.

The example involves M light pulses 100, a spatial mode selector 200, and an optical fiber 300 including N spatial modes. The spatial mode selector 200 includes spatial modes 210 and phase mask 221.

A "Phase-mask" conversion 201 is performed. The Phase-mask conversion 201 can be explained in the following way. Consider a multimode optical fiber that includes N=2 transverse modes, i.e., $HG_{0,0}$ and $HG_{1,0}$. The goal is to convert the sequence of M light pulses into the $HG_{1,0}$ mode and transmit them into the optical fiber. First, the sequence of M light pulses is made to propagate in a single mode optical fiber as the fundamental transverse mode ($HG_{0,0}$). The fundamental transverse mode at the single mode optical fiber output is expanded and collimated by a lens or lenses (collectively and individually denoted by the figure reference numeral 2100) in free space. Then, via propagation through or reflection off of a "phase mask" or "phase masks", the phase and/or amplitude of the expanded and collimated fundamental transverse mode is converted into the phase and/or amplitude of the desired spatial mode (e.g., $HG_{1,0}$). Then, the resulting spatial mode ($HG_{1,0}$) is focused into the optical fiber via another lens or lenses. The phase mask can be any of the following: (1) Glass phase plate; (2) Liquid crystal on silicon spatial light modulator; (3) Digital micro-mirror devices utilizing a micro-electro-mechanical systems; (4) multi plane light convertor; (5) "Meta-material" "q-plate"; and (6) liquid crystal "q-plate".

A "Photonic lantern" is obtained as follows. The M light pulses propagate in one or more than one single mode optical fiber of an array of N single mode optical fibers. The array of N single mode optical fibers is suitably tapered to a multimode optical fiber. The positions in the array and the core sizes of each of the single mode optical fibers are made such that the propagation of the M light pulses through one or more than one of the single mode optical fibers transforms the M light pulses into one or a superposition of N transverse spatial modes of the multimode optical fiber.

A "Core to Core" coupling is performed.

Regarding the optical fiber 300 including N spatial modes, using the spatial mode selector, the M laser pulses are coupled into an optical fiber that supports N spatial modes. An optical fiber is defined as having "core" and "cladding" regions that have indices of refraction $n_2$ and $n_1$. $n_2$ and $n_1$ need not be uniform and may be a function of position in the optical fiber.

A description will now be given regarding optical fibers to which the present invention can be applied, in accordance with an embodiment of the present invention.

Figure 4:
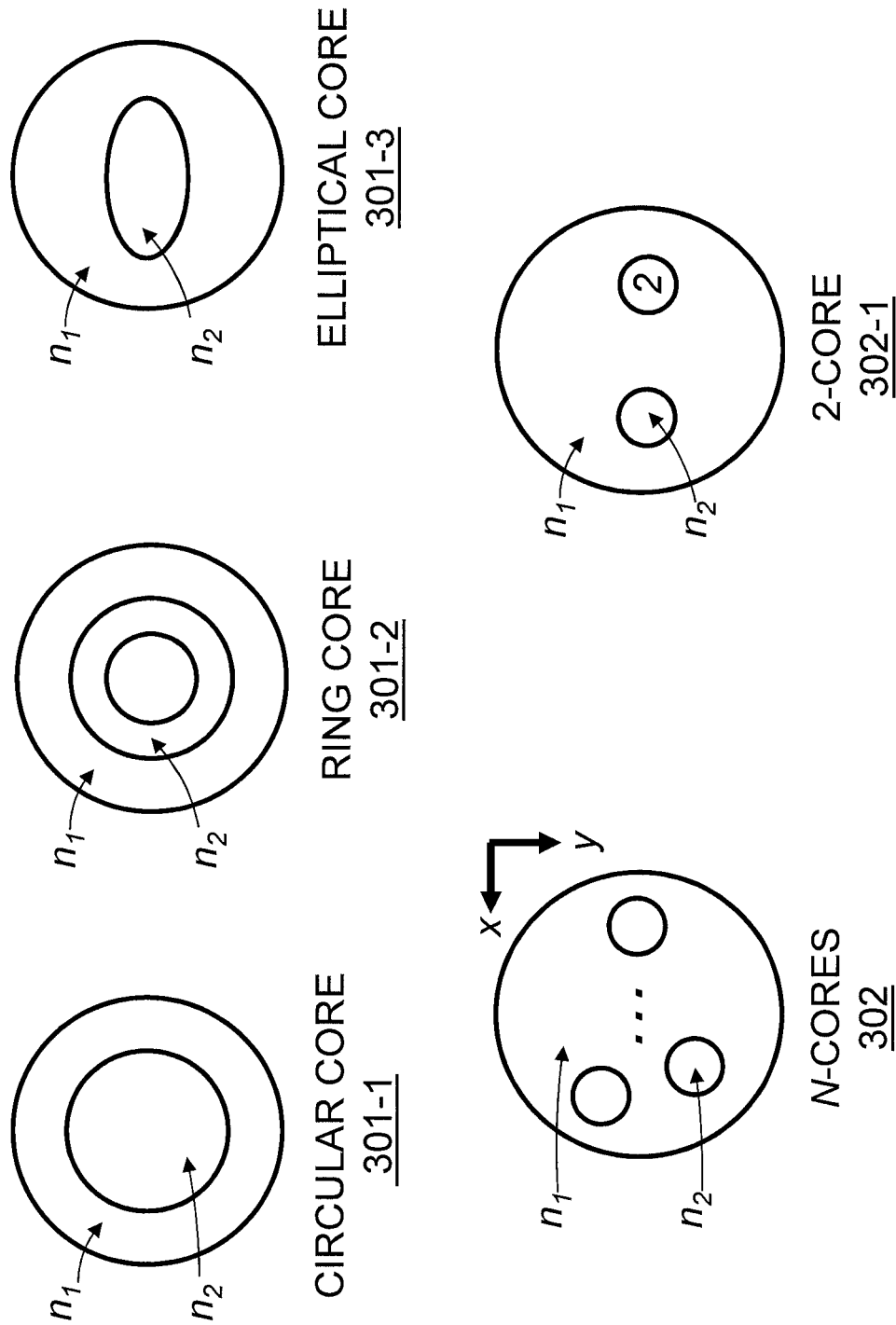
FIG. 4 shows exemplary optical fibers including N spatial modes, in accordance with an embodiment of the present invention.

Referring to FIG. 4, exemplary optical fibers including N spatial modes are shown, in accordance with an embodiment of the present invention.

A multi-mode optical fiber 301 including N transverse modes can be used. The multi-mode optical fiber can be, for example, any of the following:
(1A) multi-mode optical fiber comprising N=2 or N=3 transverse modes (i.e., a "few" mode optical fiber);
(1B) multi-mode optical fiber comprising N transverse modes w/ ~50.0 micron core radius; and
(1C) multi-mode optical fiber comprising N transverse modes w/ ~62.5 micron core radius.

A multicore optical fiber 302 including N cores can be used. The multicore optical fiber can be any of the following:
(2A) multicore optical fiber 302-1 including N=2 cores where each core includes only the fundamental transverse mode;
(2B) multicore optical fiber 302-2 including N cores where each core includes only the fundamental transverse mode; and
(2C) multicore optical fiber comprising N cores where each core includes only the fundamental transverse mode or more than one transverse mode.

A multimode or multicore optical fiber can be used that has a circular or non-circular core and index of refraction that varies as a function of position in the optical fiber. The involved geometries can include any of the following:

(3A) circular core 301-1 with step or graded index variation;
(3B) ring core 301-2 with step or graded index variation;
(3C) elliptical core 301-3 with step or graded index variation; and
(3D) so forth.

A description will now be given regarding Distributed Mode Coupling (DMC) as per step 310 of FIG. 2, in accordance with an embodiment of the present invention.

At least two of the spatial modes of the optical fiber experience distributed mode coupling (DMC). DMC can be defined in the following way:

Consider an ideal multimode optical fiber that comprises two spatial modes: spatial mode A and spatial mode B. An ideal multimode optical fiber is free from imperfections, i.e., the index of refraction profile, core/cladding size, and core/cladding shape do not vary as a function of position along the optical fiber.

Consider a light pulse that is launched into the optical fiber as spatial mode A. In this idealization, spatial mode A would not exchange power with spatial mode B as it propagates along the optical fiber. At the optical fiber output, power would be measurable in only spatial mode A.

However, in practice, an optical fiber is non-ideal and will have imperfections, such as, micro-bending. Moreover, the imperfections can be considered to be distributed along the optical fiber. Therefore, when a light pulse is launched into a non-ideal optical fiber as spatial mode A, as it propagates along the optical fiber it distributively couples power to spatial mode B. At the optical fiber output, power would be measurable in spatial mode A and spatial mode B. The distributive coupling of power from one spatial mode to another in a multimode optical fiber due to optical fiber imperfections is referred to as DMC.

The ratio of the powers of spatial mode A and spatial mode B due to DMC is referred to as the mode coupling ratio. Since mode coupling is distributive, the spatial mode coupling ratio can be defined per unit length. For example, the spatial mode coupling ratio between two transverse modes per unit length can be ~−40 dB/km. Note that the mode coupling ratio can be controlled (>−40 dB/km or <−40 db/km) by engineering the optical fiber's parameters.

A description will now be given regarding Differential Mode Delay (DMD) as per step 320 of FIG. 2, in accordance with an embodiment of the present invention.

Figure 5:
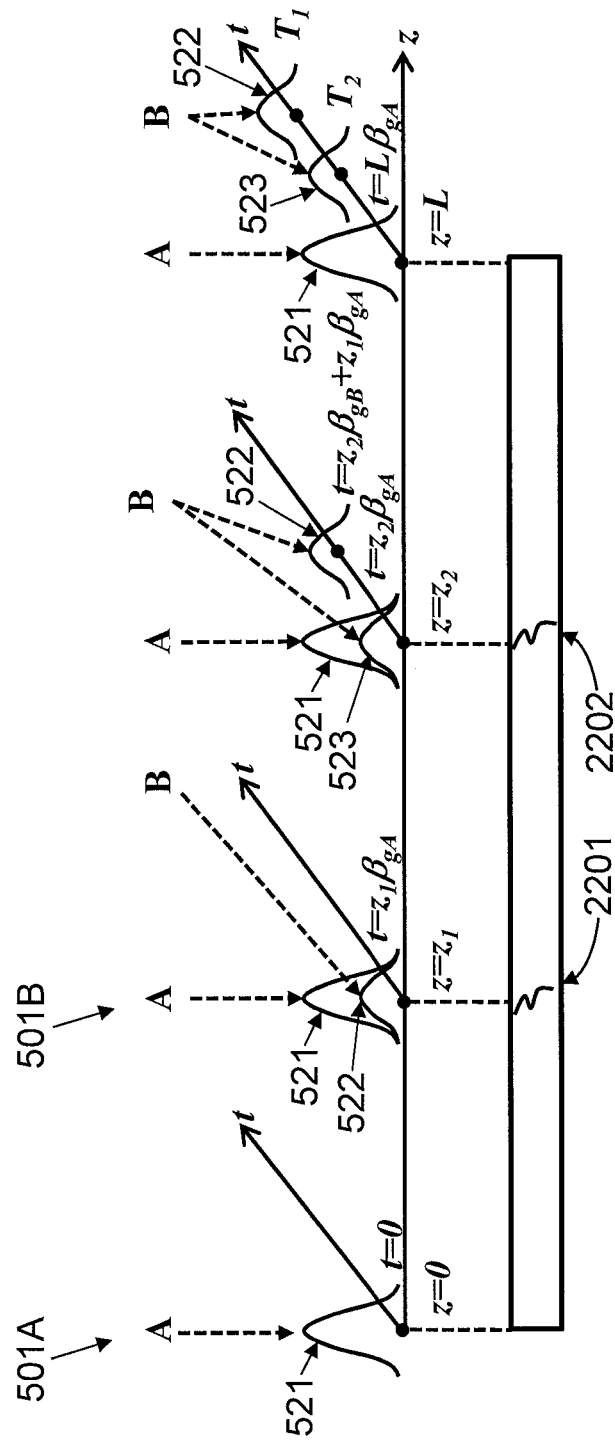
FIG. 5 shows a Distributed Mode Coupling (DMC) and Distributed Mode Delay (DMD) between spatial modes in a multimode optical fiber including N spatial modes, in accordance with an embodiment of the present invention.

At least two of the spatial modes of the optical fiber experience differential mode delay (DMD). DMD can be defined in the following way, e.g., with respect to FIG. 5. Referring to FIG. 5, a Distributed Mode Coupling (DMC) and Distributed Mode Delay (DMD) between spatial modes in a multimode optical fiber including N spatial modes is shown, in accordance with an embodiment of the present invention.

As shown in FIG. 5, consider a non-ideal multimode optical fiber that comprises two spatial modes: spatial mode A and spatial mode B. Consider that a light pulse is launched into the optical fiber input as a superposition of spatial mode A and spatial mode B. In general, the spatial modes of an ideal and non-ideal multimode optical fiber have different group velocities, i.e., spatial mode A and spatial mode B have different group velocities given by $v_{gA}$ and $v_{gB}$, respectively. Due to their different group velocities, when propagating to a position z along the optical fiber, spatial mode A and spatial mode B will arrive at z at different times given by $t=z\beta_{gA}$ and $t=z\beta_{gB}$, respectively, where $\beta_{gA}=1/v_{gA}$ and $\beta_{gB}=1/v_{gB}$. The difference in the arrival times of spatial mode A and spatial mode B at a position z is referred to as the DMD.

As shown in FIG. 5, consider any point along the optical fiber given by z at time t. The length of the optical fiber is z=L. Consider two discrete points along the fiber: $z=z_1$ and $z=z_2$. At $z_1$ and $z_2$ there is DMC due to imperfections, i.e., power from spatial mode A is exchanged with spatial mode B.

At z=0 and t=0, a light pulse 521 is launched into the optical fiber as spatial mode A 501A.

The light pulse 521 propagates to $z=z_1$ at $t=z_1\beta_{gA}$. Due to an imperfection 2201 at $z=z_1$, there is DMC 501B, i.e., power from spatial mode A is exchanged with spatial mode B, producing a first new light pulse 522.

Due to their different group velocities, the original light pulse 521 and the first new light pulse 522 propagate to $z=z_2$ at $t=z_2\beta_{gA}$ and $t=z_2\beta_{gB}+z_1\beta_{gA}$, respectively. Due to another imperfection 2202 at $z=z_2$, there is DMC 501C, i.e., power from spatial mode A is exchanged with spatial mode B, producing a second new light pulse 523.

Again, due to their different group velocities, the original light pulse 521, the first new light pulse 522, and the second new light pulse 523 propagate to the optical fiber output (z=L) at different times given (thus there is DMD 501D), respectively, by $t=L\beta_{gA}$, $$T_1 = z_1\beta_{gA} + (L-z_1)\beta_{gB}, \quad (1)$$

and $$T_2 = z_2\beta_{gA} + (L-z_2)\beta_{gB}, \quad (2)$$

As a result, due to the combination of DMC and DMD, at the optical fiber output, two new light pulses (522 and 523) are produced at $z_1$ and $z_2$ and arrive at the optical fiber output as spatial mode B at two different times given by $T_1$ and $T_2$. The resulting time delay at the optical fiber output between the two new light pulses is given by the following equation:

$$\Delta T = T_2 - T_1 \quad (3)$$
$$= \Delta z \Delta \beta_g,$$

where $\Delta z = z_2 - z_1$ and $\Delta\beta_g = \beta_{gB} - \beta_{gA}$.

Effectively, the positions $z_1$ and $z_2$ along the optical fiber can be identified via a time of flight analysis of spatial mode B at the optical fiber output. Note that $\Delta\beta_g$ can be controlled by engineering the optical fiber's parameters.

Figure 6:
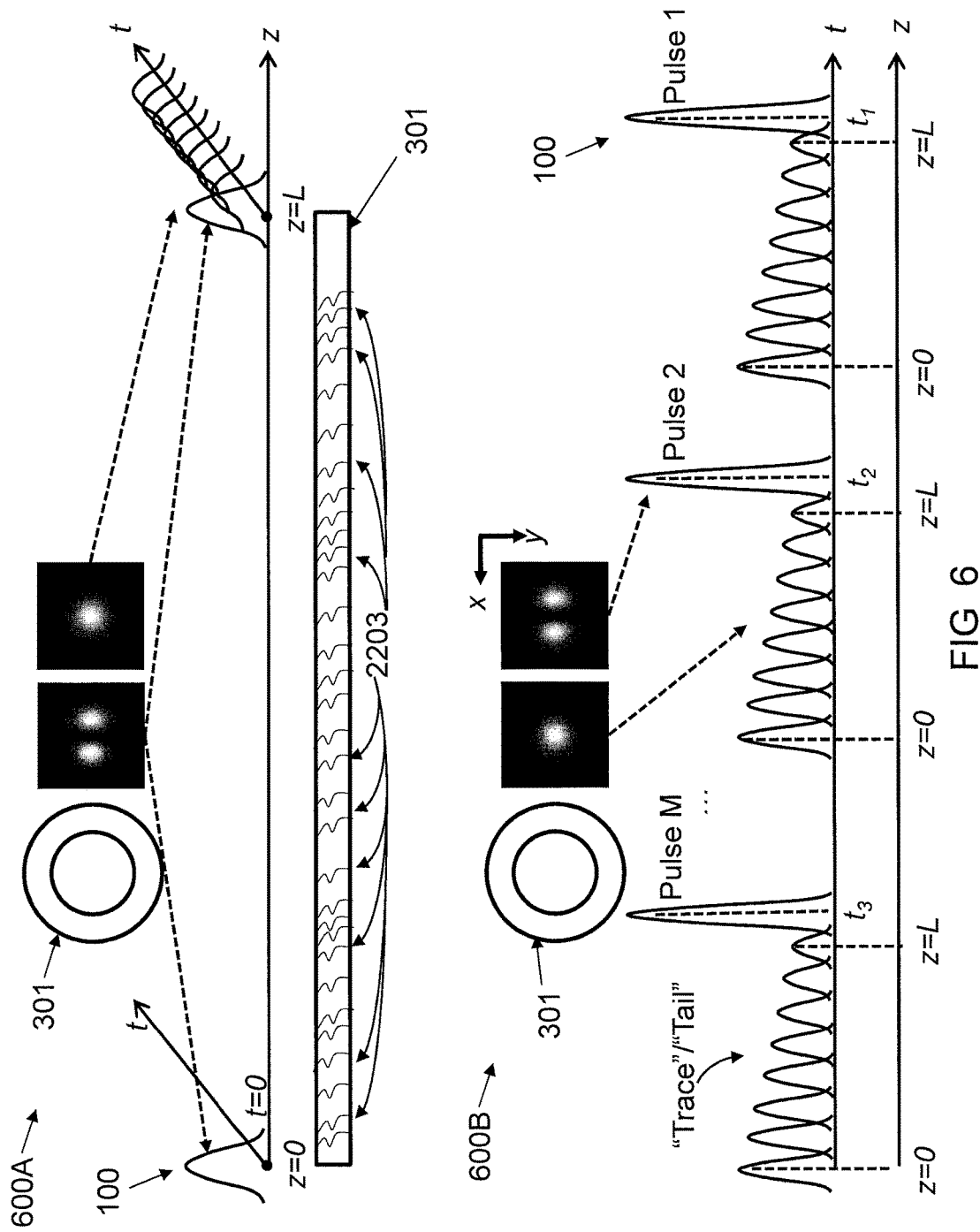
FIG. 6 shows a "tail"/"trace" acquired by the M light pulses due to DMC and DMD between transverse modes in a multimode optical fiber that includes N=2 transverse modes, in accordance with an embodiment of the present invention.

A further description will now be given regarding step 330 of FIG. 2, with reference to FIGS. 2, 5, and 6. Referring to FIG. 6, a "tail"/"trace" acquired by the M light pulses due to DMC and DMD between transverse modes in a multi-mode optical fiber that includes N=2 transverse modes is shown, in accordance with an embodiment of the present invention.

As noted above, step 330 involves acquiring "tails"/"traces", by the M light pulses (due to DMC (step 515A) and DMD (step 515B)).

In reality, in contrast to FIG. 5, optical fiber imperfections do not occur at discrete positions z along the optical fiber. Instead, optical fiber imperfections are uniformly distributed along the optical fiber's length, as shown in FIG. 6. While optical fiber imperfections are random, it should be understood that imperfections at different optical fiber positions have the same randomness. As a result, with respect to FIG. 5, due to the combination of DMC and DMD, when launching a light pulse into the optical fiber as spatial mode A, at the optical fiber output, in the time domain, spatial mode B will comprise a "trail"/"trace" of light pulses produced continuously. The "trail" or "trace" is analogous to the "time trace" of an OTDR measurement.

The "trail"/"trace" that each of the M light pulses acquires can be explained by using an example of a multimode optical fiber that comprises N=2 transverse modes: $HG_{0,0}$ and $HG_{1,0}$, as shown in FIG. 6. As shown in FIG. 6 with respect to reference numeral 600A, when a light pulse is transmitted at the optical fiber input as the $HG_{1,0}$ mode, at the optical fiber output, because there are imperfections 2203 at every point z along the optical fiber, and therefore the combination of DMC and DMD at every point z along the optical fiber, in the time domain, the light pulse will acquire a "trail"/"trace" of light pulses that are the $HG_{0,0}$ mode. As shown in FIG. 6 with respect to reference numeral 600B, when transmitting a sequence of M light pulses at the optical fiber input, each light pulse will acquire a "trail"/"trace" of light pulses. The first light pulse of the "trail"/"trace" corresponds to the beginning of the optical fiber (z=0). The last light pulse of the "trail"/"trace" corresponds to the end of the optical fiber (z=L), i.e., the duration of the "trail"/"trace" in the time domain corresponds the total length of the optical fiber in the space domain. In turn, each position z of the optical fiber can be discriminated via a time domain analysis of each "trail"/"trace" of each of the M light pulses that are transmitted into the optical fiber.

A further description will now be given regarding step 340 of FIG. 2, with reference to FIGS. 2 and 7.

As noted above, step 340 involves acoustic vibration changing the phases of the M light pulses.

Acoustic vibrations that make physical contact at any position(s) z along the optical fiber. The acoustic vibrations change the phases of the light pulses comprising the "tails"/"traces" of each of the light pulses in the sequence of M light pulses.

Figure 7:
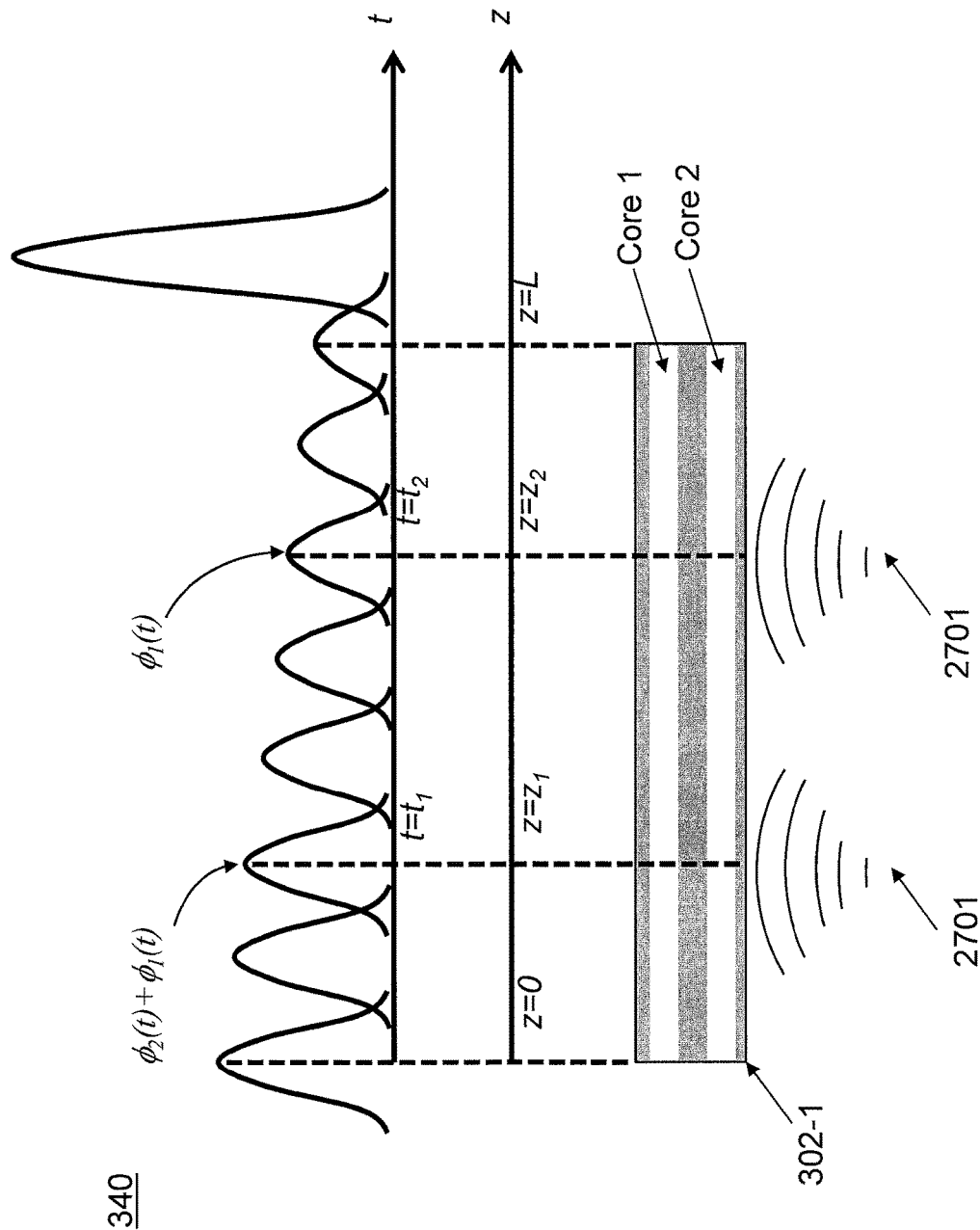
FIG. 7 shows a light pulse at the output of a 2-core optical fiber that was transmitted into the optical fiber input, in accordance with an embodiment of the present invention.

For example, consider FIG. 7. FIG. 7 shows a light pulse at the output of a 2-core optical fiber that was transmitted into the optical fiber input, in accordance with an embodiment of the present invention. Due to DMC and DMD, in turn, due to continuous imperfections along the optical fiber's length z, the light pulse acquires a "tail"/"trace". As shown in FIG. 7, acoustic vibrations 2701 make physical contact with the optical fiber at $z=z_1$ and $z=z_2$. Due to the acoustic vibrations 2701, the phases of each of the light pulses in the sequence of M light pulses will change in response to the acoustic vibrations. Because the acoustic vibrations 2701 vary as a function of time, the phases of the each light pulses in the sequence of M light pulses will vary as a function of time t. In general, the phase acquired by a light pulse in the sequence of M light pulses due to an acoustic vibration is given by $\phi(t)$.

For example, as shown in FIG. 7, because the light pulse at time $t_2$ in the "tail"/"trace" was generated at $z=z_2$, it "sees" the acoustic vibration at $z=z_2$ and acquires a phase given by $\phi_2(t)$. In contrast, because the light pulse at time $t_1$ in the "tail"/"trace" was generated at $z=z_1$, it propagates through $z=z_1$ and $z=z_2$. As a result, it "sees" the acoustic vibrations at $z=z_1$ and $z=z_2$ and acquires a phase given by given by $\phi_2(t)+\phi_1(t)$. Note that the phase acquired by light at any time in the "tail"/"trace" is a sum of the phases it acquired at all corresponding positions along the optical fiber preceding that time.

The optical fiber can make direct physical contact with the acoustic perturbation or the acoustic vibration or the acoustic vibration can be transferred to the optical fiber via an intermediate medium or device.

Any other environmental perturbation can make physical contact at any position(s) z along the optical fiber. An environmental perturbation can be any of the following: (1) acoustic vibration; (2) temperature change; (3) strain/pressure change; (4) non-acoustic vibration; and (5) optical fiber bending.

The optical fiber that experiences an environmental perturbation can be placed inside of, attached to the surface of, or in proximity to any of the following: (1) bridges; (2) tunnels; (3) railroads; (4) buildings; (5) roads, highways, streets, and sidewalks; (6) oil/gas wells terrestrial, sub-terrestrial, or under-sea; (7) borders, fences, gates, walls; (8) pipelines terrestrial, sub-terrestrial, or under-sea; (9) data transmission cables terrestrial, sub-terrestrial, or under-sea; (10) electrical transmission cables terrestrial, sub-terrestrial, or under-sea; (11) electrical generators, turbines, motors; and (12) so forth.

A further description will now be given regarding step 400 of FIG. 2.

As noted above, step 400 involves receiving the M light pulses, by the spatial mode selector at the optical fiber input/output.

The sequence of M light pulses are "spatially filtered" to be one spatial mode or a superposition of N spatial modes using a spatial mode selector. Effectively, the "tails"/"traces" of the M light pulses, which are at least one spatial mode, can be "spatially filtered" from the original M light pulses.

The spatial mode selector "spatially filters" the sequence of M light pulses into one spatial mode or a superposition of N spatial modes using free space optic or fiber optics or a combination of free space optics and fiber optics. The spatial mode convertor can be any of the following.

(1) "Phase-mask" conversion: Phase-mask conversion can be explained in the following way. Consider a multi-mode optical fiber that comprises N=2 transverse modes, i.e., $HG_{0,0}$ and $HG_{1,0}$. The goal is to "spatially filter" the sequence of M light pulses into the $HG_{0,0}$ mode at the optical fiber output. At the optical fiber output, the light is expanded and collimated by a lens or lenses in free space. Then, the light is made to propagate through or reflect off of a "phase mask" or "phase masks" displays the phase and/or amplitude of the HG mode ($HG_{0,0}$) that is to be spatially filtered. Then, the light is focused into a single mode optical fiber via another lens or lenses. Via focusing into the single mode optical fiber, the light is "spatially filtered" in the $HG_{0,0}$ modes. The phase mask can be any of the following: (1A) glass phase plate; (1B) liquid crystal on silicon spatial light modulator; (1C) digital micro-mirror devices utilizing a micro-electro-mechanical systems; (1D) multi-plane light convertor; (1E) "Meta-material" "q-plate"; and (1F) liquid crystal "q-plate".

(2) "Photonic lantern": The optical fiber is suitably tapered to an array of N single mode optical fibers. The M light pulses propagate in one or more than one single mode optical fiber of an array of N single mode optical fibers. The positions in the array and the core sizes of each of the single mode optical fibers are made such that the propagation of the M light pulses through one or more than one of the single mode optical fibers transforms the M light pulses into one or a superposition of N transverse spatial modes at the output of one or more than one the single mode optical fiber.

(3) "Core to Core" coupling.

A further description will now be given regarding step 500 of FIG. 2.

As noted above, step 500 involves performing a phase measurement of the M light pulses "tails"/"traces".

After the spatial mode selector, the phases of the M light pulses' "tails"/"traces" are measured. The phases can be measured by any method that can effectively measure the phase of light. This includes any of the following:

(1) Homodyne interferometry with self-interference, i.e., the light is interfered with a time-delayed version of itself.
(2) Heterodyne interferometry with self-interference, i.e., the light is interfered with a time delayed and frequency shifted version of itself.
(3) Homodyne or heterodyne interferometry with a local oscillator, i.e., the light interfered with another light source.

Figure 8:
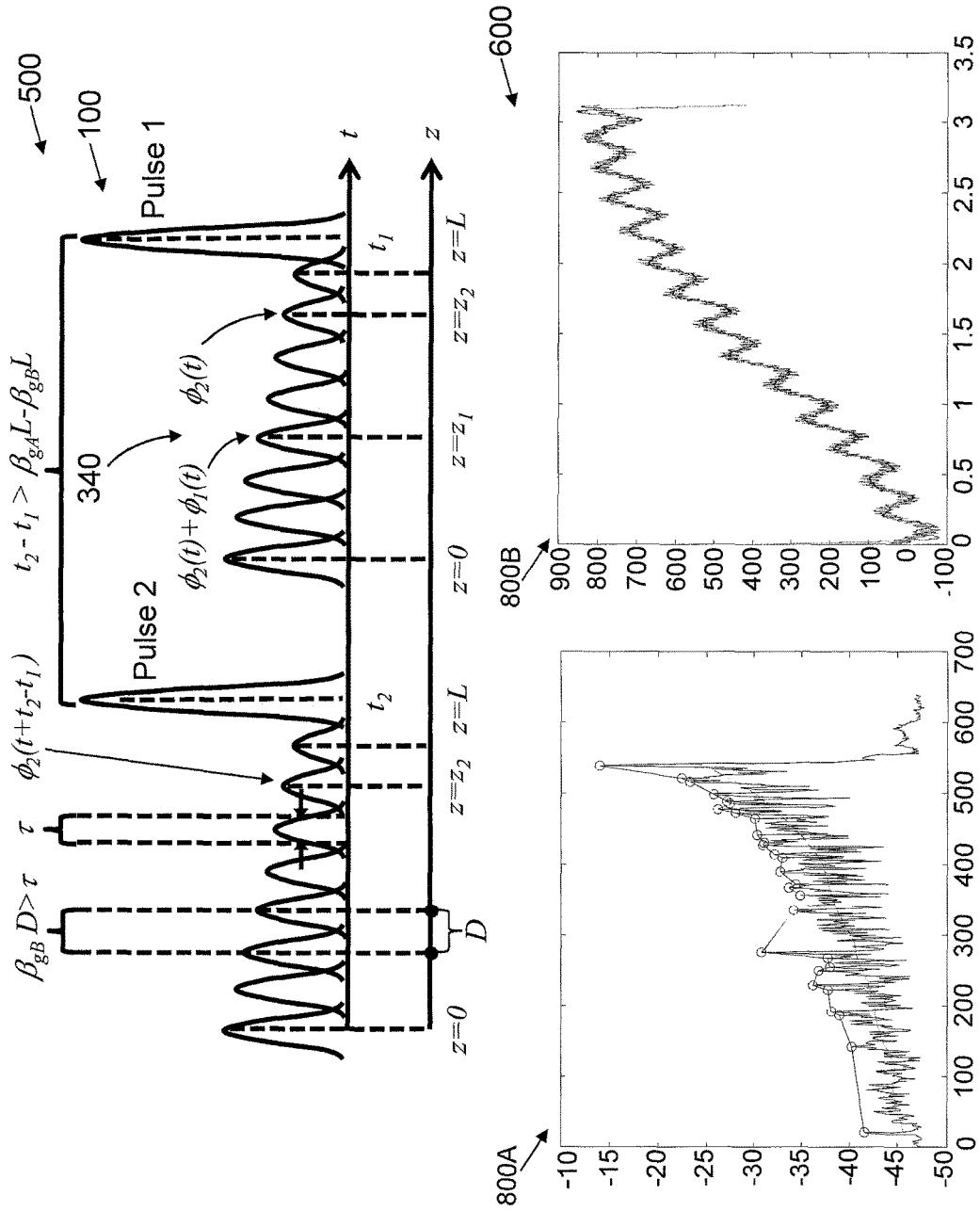
FIG. 8 shows tune/frequency domain analysis of the "tails"/"traces" of the M light pulses, in accordance with an embodiment of the present invention.

The phases can be determined by comparison with another light source or by comparison with another light pulse of the "tail"/"trace". For example, the measured phases of the light pulses of an experimentally measured "tail"/"trace" is shown in plot 800A of FIG. 8. FIG. 8 shows tune/frequency domain analysis of the "tails"/"traces" of the M light pulses, in accordance with an embodiment of the present invention.

A further description will now be given regarding step 600 of FIG. 2.

As noted above, step 600 involves performing a time/frequency domain analysis of the M light pulses "tails"/"traces" using distributed sensing of acoustic vibrations along optical fiber.

Figure 9:
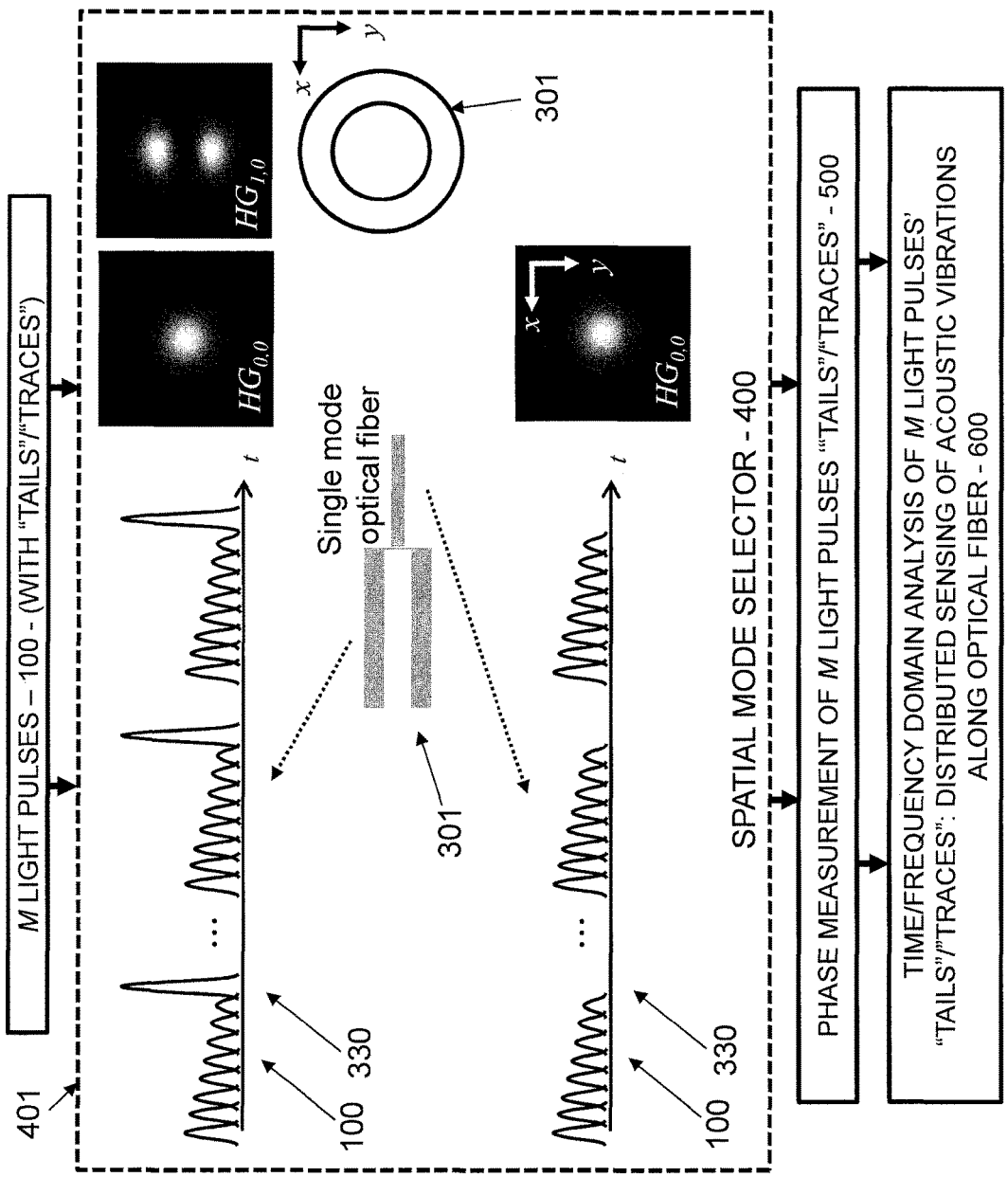
FIG. 9 shows two light pulses of a sequence of M light pulses at the output of an optical fiber that comprises two spatial modes, in accordance with an embodiment of the present invention.

The M light pulses are analyzed in the time/frequency domain. For example, consider FIG. 9. FIG. 9 shows two light pulses of a sequence of M light pulses at the output of an optical fiber that comprises two spatial modes: spatial mode A and spatial mode B. At the optical fiber input, the sequence of M light pulses was transmitted as spatial mode A. Due to DMC and DMD, a "trail"/"tail" of light pulses for each light pulse of the sequence of M light pulses was generated as spatial mode B.

As described above, due to DMC and DMD, each light pulse of the "trail"/"tail" of light pulses correspond to a position z along the optical fiber.

The maximum resolution between to positions z along the optical fiber is explained as follows. A light pulse must acquire a DMD at least equal to the value of its pulse width τ so that it can be unambiguously discriminated from an adjacent light pulse in time (i.e. they do not overlap). The pulse width τ is a value of time. In turn, the pulse width τ corresponds to a light pulse propagating a distance $D=\tau/\beta_{gB}$. Because, a light pulse must acquire a DMD at least equal to the value its pulse width τ so that it can be unambiguously discriminated from an adjacent light pulse in time (i.e., they do not overlap) and because each light pulse of the "trail"/"tail" of light pulses correspond to a position z along the optical fiber, the maximum resolution between two position z along the optical fiber is given by the $D=\tau/\beta_{gB}$. Therefore, the DMD and the pulse width τ determine the resolution between two positions z along the optical fiber.

Furthermore, the repetition rate of the sequence of M pulses, i.e., the time between each pulse in the sequence, must be larger than the time of flight a light pulse as spatial mode A or spatial mode B so that the "tail"/"trace" of each light pulse can be unambiguously discriminated, i.e., it does not overlap with an adjacent "tail"/"trace". Because the time of flight a light pulse as spatial mode A or spatial mode B is given by $L\beta_{gA}$ and $L\beta_{gB}$, respectively, the repetition rate of the sequence of M pulses, i.e., the time between each pulse in the sequence, must be larger than time difference between the delay at the optical fiber output of the original light pulse, $L\beta_{gA}$, and that of the last light pulse in the "tail"/"trace", $L\beta_{gB}$, i.e., $t_2-t_1 > L\beta_{gA} - L\beta_{gB}$.

When an acoustic vibrations makes physical contact with the optical fiber at $z=z_1$ and $z=z_2$ the phases of the each light pulses in the sequence of M light pulses will change in response to the acoustic vibrations. Because the acoustic vibration varies as a function of time, the phases of the each light pulses in the sequence of M light pulses will vary as a function of time t. In general, the phase acquired by a light pulse in the sequence of M light pulses due to an acoustic vibration is given by $\phi(t)$.

For example, referring to FIG. 8, because the light pulse at time $t_2$ in the "tail"/"trace" was generated at $z=z_2$, it "sees" the acoustic vibration at $z=z_2$ and acquires a phase given by $\phi_2(t)$. In contrast, because the light pulse at time $t_1$ in the "tail"/"trace" was generated at $z=z_1$, it propagates through $z=z_1$ and $z=z_2$. As a result, it "sees" the acoustic vibrations at $z=z_1$ and $z=z_2$ and acquires a phase given by given by $\phi_2(t)+\phi_1(t)$. Note that the phase acquired by light at any time in the "tail"/"trace" is a sum of the phases it acquired at all corresponding positions along the optical fiber preceding that time.

Because a given light pulse of the "tail"/"trace" corresponds to a position z along the optical fiber, and because the light pulse's phase will change when the optical fiber experiences an acoustic vibration, the change of that light pulse's phase in time can used to determine the signal of the acoustic vibration, i.e., the acoustic vibration's amplitude and frequency. For example, the measured change in time of the phase of one light pulse of an experimentally measured "tail"/"trace" is shown in plot 800B of FIG. 8.

The time dependent phase change of the light pulse can be analyzed via a time/frequency domain analysis. A time/frequency domain analysis comprises an analysis of the measured phases of the light pulses in the "tail"/"trace" corresponding to a position z for every sequential light pulse in the sequence of M light pulses, e.g., as shown in FIG. 9, analyzing the phase of the light pulses at times $t+t_2-t_1$ and t for the light pulse corresponding to position $z_2$ for light pulse 2 and light pulse 1, respectively, A time/frequency domain analysis can include any method with which a time-periodic signal (frequency) can be identified from the time dependent phase change of the light pulse. This includes, a Fourier transform, or any comparable mathematical methods.

Note that well-known "optical frequency domain reflectometry" (OFDR) methods can also be used.

Figure 10:
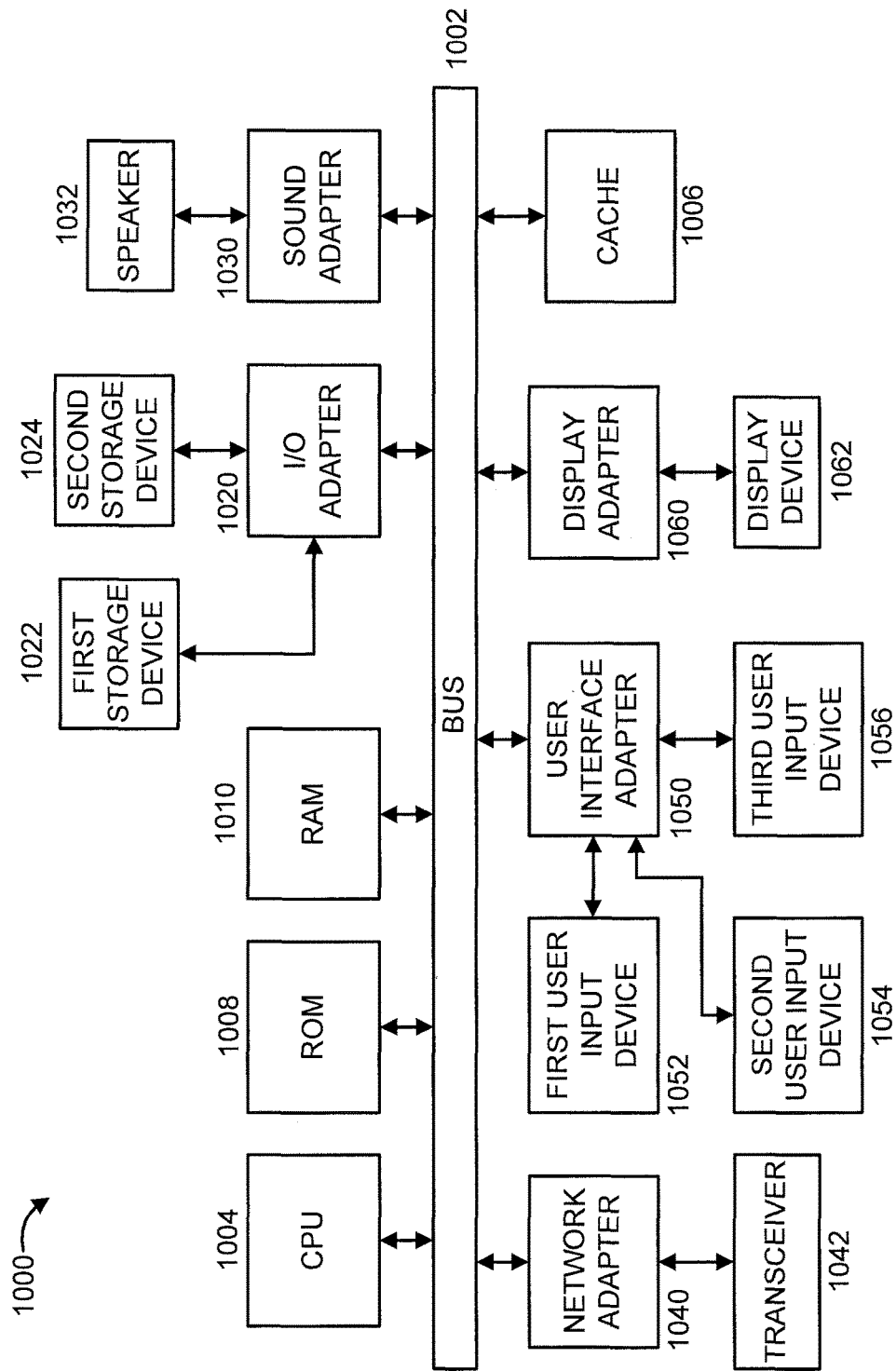
FIG. 10 shows an exemplary processing system to which the present principles may be applied, in accordance with an embodiment of the present principles.

Referring to FIG. 10, an exemplary processing system 1000 to which the present principles may be applied is shown, in accordance with an embodiment of the present principles. The processing system 1000 includes at least one processor (CPU) 1004 operatively coupled to other components via a system bus 1002. A cache 1006, a Read Only Memory (ROM) 1008, a Random Access Memory (RAM) 1010, an input/output (I/O) adapter 1020, a sound adapter 1030, a network adapter 1040, a user interface adapter 1050, and a display adapter 1060, are operatively coupled to the system bus 1002.

A first storage device 1022 and a second storage device 1024 are operatively coupled to system bus 1002 by the I/O adapter 1020. The storage devices 1022 and 1024 can be any of a disk storage device (e.g., a magnetic or optical disk storage device), a solid state magnetic device, and so forth. The storage devices 1022 and 1024 can be the same type of storage device or different types of storage devices.

A speaker 1032 is operatively coupled to system bus 1002 by the sound adapter 1030. A transceiver 1042 is operatively coupled to system bus 1002 by network adapter 1040. A display device 1062 is operatively coupled to system bus 1002 by display adapter 1060.

A first user input device 1052, a second user input device 1054, and a third user input device 1056 are operatively coupled to system bus 1002 by user interface adapter 1050. The user input devices 1052, 1054, and 1056 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 1052, 1054, and 1056 can be the same type of user input device or different types of user input devices. The user input devices 1052, 1054, and 1056 are used to input and output information to and from system 1000.

Of course, the processing system 1000 may also include other elements (not shown), as readily contemplated by one of skill in the art, as well as omit certain elements. For example, various other input devices and/or output devices can be included in processing system 1000, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 1000 are readily contemplated by one of ordinary skill in the art given the teachings of the present principles provided herein.

Figure 11:
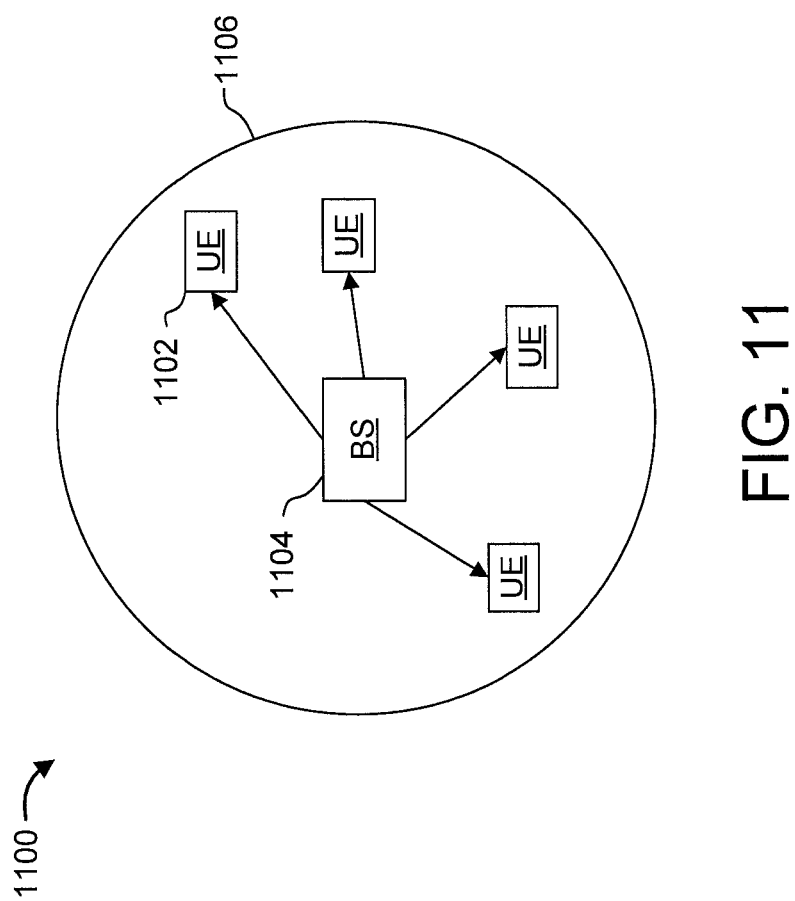
FIG. 11 shows an exemplary Multi-User Multiple Input Multiple Output (MU-MIMO) telecommunication system in which embodiments of the present invention may be implemented.

Moreover, it is to be appreciated that system 1100 described below with respect to FIG. 11 is a system for implementing respective embodiments of the present principles. Part or all of processing system 1000 may be implemented in one or more of the elements of system 1100.

Further, it is to be appreciated that processing system 1000 may perform at least part of the method described herein including, for example, at least part of the method of FIG. 2. Similarly, part or all of system 1100 may be used to perform at least part of the method of FIG. 2.

Referring to FIG. 11, an exemplary Multi-User Multiple Input Multiple Output (MU-MIMO) telecommunication system 1100 in which embodiments of the present invention may be implemented is shown. In the downlink of system 1100, multiple scheduled users (UEs) 1102 in a cell 1106 are simultaneously served by a base station (BS) 1104. In the MU-MIMO downlink from the BS 1104, each user is served a data stream in accordance with a schedule determined by the present invention. For example, the schedule can be determined based on maximizing a difference between two submodular set functions applied over a ground set of virtual users, as further described herein below. In this way, gains can be achieved over prior art scheduling approaches while maintaining reasonable complexity.

Figure 12:
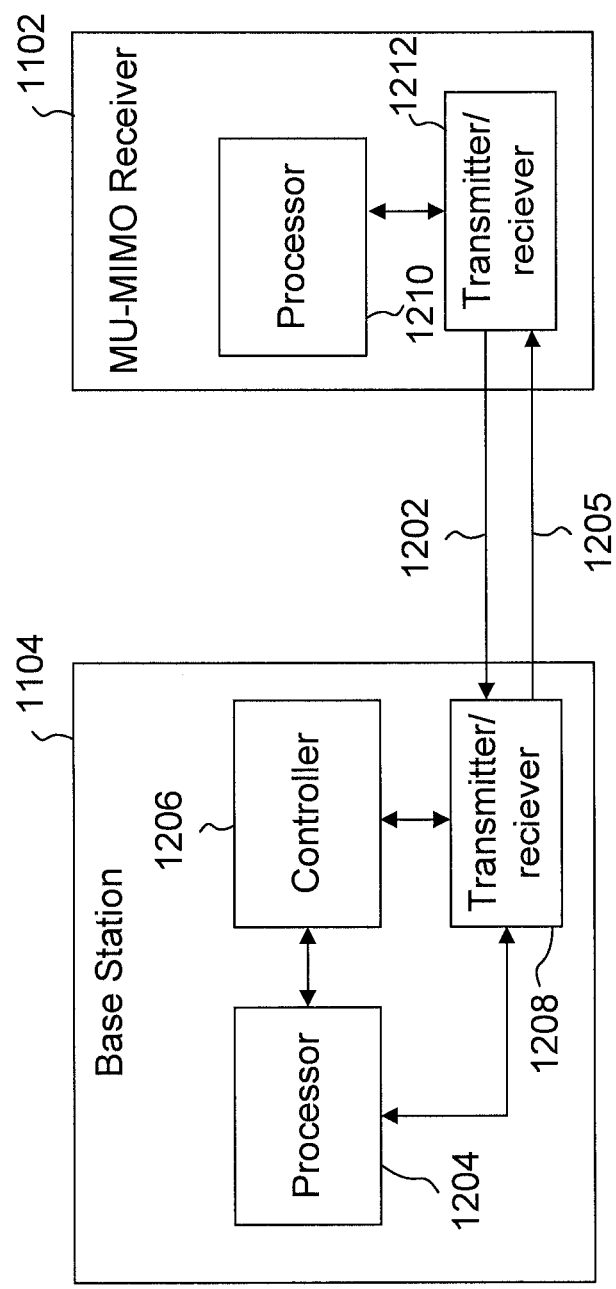
FIG. 12 shows exemplary implementations of a base station system and a MU-MIMO receiver system, in accordance with an embodiment of the present invention.

Referring to FIG. 12, with continuing reference to FIG. 11, exemplary implementations of a base station system 1104 and a MU-MIMO receiver system 1102 are shown. The base station 1104 may include a scheduler 1204 and a processor 1206, while the user 1102 can include processor 1210. The processor 1206 and processor 1210 can use respective storage mediums provided in the base station 1104 and receiver 1102. In addition, the base station 1104 and the receiver 1102 can include transmitters/receivers 1208 and 1212, respectively, for the transmission and reception of control signals. The user 1102 can transmit control signals to the base station 1104 on one or more uplink control channels 1202 and the base station 1104 can transmit control signals to the user 1102 on one or more downlink control channels 1205.

A description will now be given regarding some of the many attendant competitive values/advantages of the present invention over the prior art.

While some prior art (increasing power, Raman amplification, etc.) can address the problems of DAS described above, i.e., detection speed, distance, and sensitivity, such prior art relies on Rayleigh backscattering. The fundamental limits of conventional methods of DAS are dictated by Rayleigh scattering, i.e., only one laser pulse can propagate in the optical fiber at any time and the power of Rayleigh scattering is significantly weaker than that of the laser pulse. As a result, such prior art can only marginally improve conventional methods of DAS as they do not remove the fundamental limits; they merely "push" the limits a little bit further.

In contrast, this invention is a method of DAS that does not rely on Rayleigh backscattering. As a result, the fundamental limitations imposed by conventional methods of DAS that rely on Rayleigh scattering are removed. This invention relies on different physical phenomena, i.e., distributed mode coupling and distributed mode delay. The fundamental limits associated with distributed mode coupling and distributed mode delay are order of magnitude higher than those of conventional methods of DAS that rely on Rayleigh scattering. With this invention, oil/gas pipelines/well can be monitored with order of magnitude increased detection Speed, Increased Distance, and Increased Sensitivity.

The competitive/commercial value of this invention is that, due to its reliance on distributed mode coupling and distributed mode delay instead of Rayleigh scattering, not only can this invention compete with existing applications of DAS, it can also be used in new application spaces where conventional methods of DAS cannot.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable medium such as a semiconductor or solid state memory, magnetic tape, a removable computer diskette, a random access memory (RAM), a read-only memory (ROM), a rigid magnetic disk and an optical disk, etc.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope and spirit of the invention as outlined by the appended claims. Having thus described aspects of the invention, with the details and particularity required by the patent laws, what is claimed and desired protected by Letters Patent is set forth in the appended claims.

What is claimed is:

1. A system for distributed acoustic sensing in a multimode optical fiber, comprising:
    a transmitter for simultaneously propagating a sequence of M light pulses through the multimode optical fiber using a spatial mode selected from a set of N spatial modes provided by a spatial mode selector for the transmitter that is coupled to an input to the multimode optical fiber, with M and N being respective integers greater than one; and
    a receiver for receiving the sequence of M light pulses at an output of the multimode optical fiber and detecting an environmental perturbation in the multimode optical fiber based on an evaluation of a propagation of the sequence of M light pulses through the multimode optical fiber.

2. The system of claim 1, wherein the spatial mode selector is configured to selectively provide one or more of the N spatial modes to the multimode optical fiber.

3. The system of claim 1, wherein the spatial mode selector is configured to selectively transmit the sequence of M light pulses as one or multiple higher order spatial modes.

4. The system of claim 3, further comprising another spatial mode selector coupled to an output of the multimode optical fiber at the receiver for receiving the sequence of M light pulses as the one or multiple higher order spatial modes.

5. The system of claim 1, wherein the spatial mode selector acquires traces of the sequence of M light pulses using Distributed Mode Coupling and Differential Mode Delay.

6. The system of claim 1, wherein a phase of the M light pulses in the sequence is changed by the multimode optical fiber responsive to the environmental perturbation.

7. The system of claim 1, wherein the receiver comprises a phase measurement device, for the evaluation of the propagation of the sequence of M light pulses through the multimode optical fiber, that measures phases of traces acquired from the sequence of M light pulses using Distributed Mode Coupling and Differential Mode Delay.

8. The system of claim 1, wherein the receiver comprises a time domain and frequency domain analyzer, for the evaluation of the propagation of the sequence of M light pulses through the multimode optical fiber, that performs a time domain analysis and a frequency domain analysis of traces acquired from the sequence of M light pulses using Distributed Mode Coupling and Differential Mode Delay.

9. The system of claim 1, wherein the spatial mode selector provides the selected spatial mode using a phase mask conversion having a phase mask for converting a parameter of an expanded and collimated fundamental transverse mode relating to the sequence of M light pulses into a parameter of the selected spatial mode, wherein the parameter is selected from the group consisting of a phase and an amplitude.

10. A computer-implemented method for distributed acoustic sensing in a multimode optical fiber, comprising:
simultaneously propagating, by a transmitter, a sequence of M light pulses through the multimode optical fiber using a spatial mode selected from a set of N spatial modes provided by a spatial mode selector coupled to an input to the multimode optical fiber, with M and N being respective integers greater than one; and
detecting, by a receiver, an environmental perturbation in the multimode optical fiber based on an evaluation of a propagation of the sequence of M light pulses through the multimode optical fiber.

11. The computer-implemented method of claim 10, wherein the spatial mode selector is configured to selectively provide one or more of the N spatial modes to the multimode optical fiber.

12. The computer-implemented method of claim 11, wherein the spatial mode selector is configured to selectively transmit the sequence of M light pulses as the one or multiple higher order spatial modes.

13. The computer-implemented method of claim 10, wherein said detecting step comprises receiving the sequence of M light pulses as the one or multiple higher order spatial modes by another spatial mode selector coupled to an output of the multimode optical fiber.

14. The computer-implemented method of claim 10, wherein said detecting step comprises acquiring traces of the sequence of M light pulses using Distributed Mode Coupling and Differential Mode Delay.

15. The computer-implemented method of claim 10, wherein said detecting step comprises changing a phase of the M light pulses in the sequence responsive to the environmental perturbation.

16. The computer-implemented method of claim 10, wherein said detecting step comprises measuring phases of traces acquired from the sequence of M light pulses using Distributed Mode Coupling and Differential Mode Delay.

17. The computer-implemented method of claim 10, wherein said detecting step comprises performing a time domain analysis and a frequency domain analysis of traces acquired from the sequence of M light pulses using Distributed Mode Coupling and Differential Mode Delay.

18. The computer-implemented method of claim 10, wherein the spatial mode selector provides the selected spatial mode using a phase mask conversion having a phase mask for converting a parameter of an expanded and collimated fundamental transverse mode relating to the sequence of M light pulses into a parameter of the selected spatial mode, wherein the parameter is selected from the group consisting of a phase and an amplitude.

19. A computer program product for distributed acoustic sensing in a multimode optical fiber, the computer program product comprising a non-transitory computer readable storage medium having program instructions embodied therewith, the program instructions executable by a computer to cause the computer to perform a method comprising:
simultaneously propagating, by a transmitter, a sequence of M light pulses through the multimode optical fiber using a spatial mode selected from a set of N spatial modes provided by a spatial mode selector coupled to an input to the multimode optical fiber, with M and N being respective integers greater than one; and
detecting, by a receiver, an environmental perturbation in the multimode optical fiber based on an evaluation of a propagation of the sequence of M light pulses through the multimode optical fiber.

20. The computer program product of claim 18, wherein the spatial mode selector is configured to selectively provide one or more of the N spatial modes to the multimode optical fiber.

* * * * *